(12) United States Patent
Riva

(10) Patent No.: US 10,271,861 B2
(45) Date of Patent: Apr. 30, 2019

(54) 4-IN-1 FEMORAL FINISHING CUTTING JIG

(71) Applicant: Gian-Guido Riva, Bologna (IT)

(72) Inventor: Gian-Guido Riva, Bologna (IT)

(73) Assignee: Rejoint S.R.L., Bologna (IT)

( * ) Notice: Subject to any disclaimer, the term of this patent is extended or adjusted under 35 U.S.C. 154(b) by 245 days.

(21) Appl. No.: 15/292,960

(22) Filed: Oct. 13, 2016

(65) Prior Publication Data

US 2017/0105740 A1    Apr. 20, 2017

(30) Foreign Application Priority Data

Oct. 14, 2015   (IT) ......................... 102015000061621

(51) Int. Cl.
| | |
|---|---|
| *A61B 17/15* | (2006.01) |
| *A61B 17/17* | (2006.01) |
| *A61B 34/10* | (2016.01) |
| *A61B 17/56* | (2006.01) |

(52) U.S. Cl.
CPC ........ *A61B 17/1764* (2013.01); *A61B 17/155* (2013.01); *A61B 34/10* (2016.02); *A61B 2017/568* (2013.01); *A61B 2034/108* (2016.02)

(58) Field of Classification Search
CPC .................................................. A61B 17/155
See application file for complete search history.

(56) References Cited

U.S. PATENT DOCUMENTS

| | | | | |
|---|---|---|---|---|
| 2005/0234461 A1* | 10/2005 | Burdulis, Jr. | ........ | A61B 17/155 606/79 |
| 2009/0087276 A1* | 4/2009 | Rose | .................... | A61B 17/155 409/79 |
| 2009/0088763 A1* | 4/2009 | Aram | ................... | A61B 17/155 606/88 |
| 2009/0270868 A1* | 10/2009 | Park | ....................... | A61B 17/15 606/87 |
| 2010/0324692 A1* | 12/2010 | Uthgenannt | .......... | G16H 50/50 623/20.35 |
| 2012/0041446 A1* | 2/2012 | Wong | ................. | A61B 17/1703 606/96 |

(Continued)

FOREIGN PATENT DOCUMENTS

| | | |
|---|---|---|
| WO | 2011106430 A1 | 9/2011 |
| WO | 2012167016 A1 | 12/2012 |
| WO | WO 2012167016 A1 * | 12/2012 ........... A61B 17/155 |

OTHER PUBLICATIONS

Italian Search Report received in Italian Patent Application No. 102015000061621 dated May 30, 2016.

*Primary Examiner* — Zade Coley
(74) *Attorney, Agent, or Firm* — Blank Rome LLP

(57) ABSTRACT

A customised patient-specific 4-in-1 femoral finishing cutting jig comprising a cutting block which is configured to be placed, in use, in contact with the distal resection surface of a femur; the jig being characterised in that it comprises a reference means which is connected to said block; wherein the reference means is configured to position, in use, said block relative to the distal resection surface in a predetermined and patient-specific manner; wherein the reference means comprises a first contact element having a first surface which is configured to face, in use, a first femoral condyle and being customised and patient-specific; said first surface is configured to be placed against a respective portion of a first femoral condyle having a corresponding profile.

8 Claims, 2 Drawing Sheets

(56) References Cited

U.S. PATENT DOCUMENTS

2012/0265496 A1* 10/2012 Mahfouz ............... A61B 17/14
                                                    703/1
2015/0088142 A1*  3/2015 Gibson ............... A61B 17/155
                                                    606/88

* cited by examiner

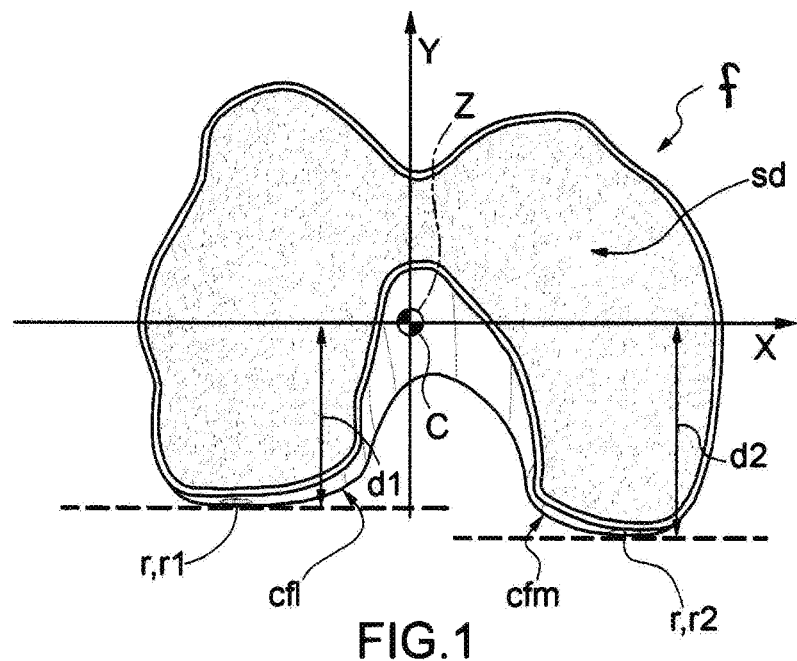
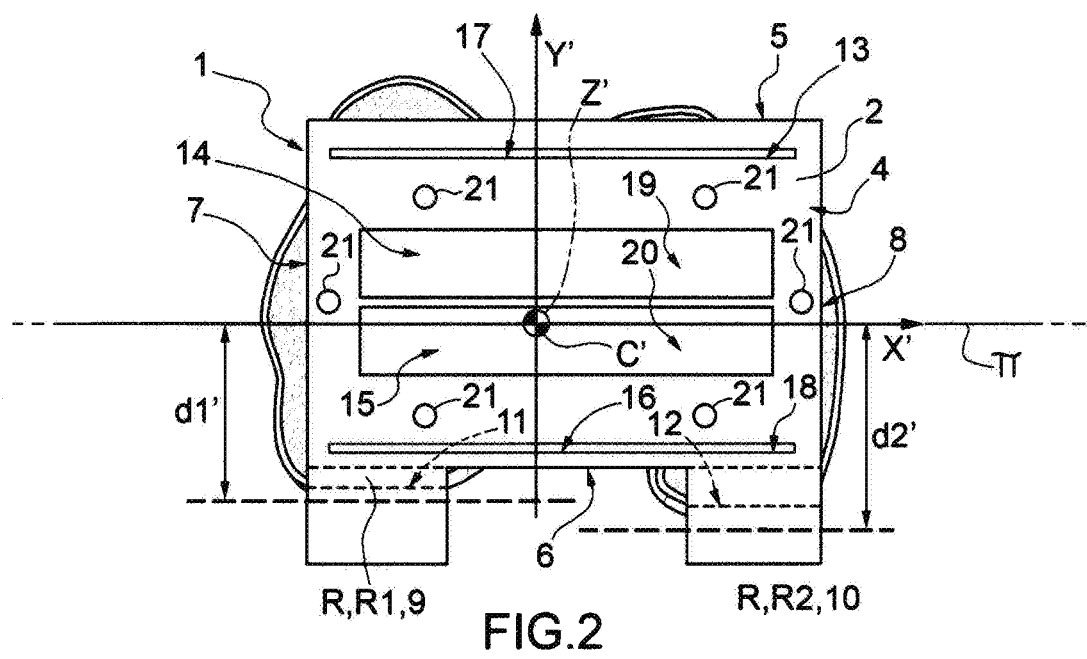

4-IN-1 FEMORAL FINISHING CUTTING JIG

The present patent application concerns a 4-in-1 femoral finishing cutting jig. In particular, the present invention concerns a customised 4-in-1 cutting jig adapted to perform anterior resection, posterior resection, anterior chamfer cut and posterior chamfer cut of the femur.

BACKGROUND OF THE INVENTION

The implant of a prosthesis to replace a damaged or worn joint is a well-known practice. In particular, for the implant of a knee prosthesis it is known that a distal resection is performed on the patient's femur and subsequently a femoral finishing which comprises the execution of an anterior resection, a posterior resection, an anterior chamfer cut and a posterior chamfer cut. During execution of the femoral finishing, correct performance of the resections and chamfer cuts is a decisive factor for correct positioning of the prosthesis. Furthermore, the inclinations imparted to the bone resection surfaces and to the chamfer cuts determine postural corrections of the joint, for example the intra- or extra-rotation of the knee.

To carry out the femoral finishing, it is known that multipurpose metal instruments are used (also called 4-in-1 cutting jigs) which adapt to the distal femoral part and are configured to guide, in use, sickle blades. These metal instruments can be re-used several times on different patients and the correct positioning of the metal instruments substantially depends on the ability of the surgeon at the time of the operation. In particular, during the operation, the surgeon has to manually adjust the positioning of the instruments to obtain a desired intra- or extra-rotation of the joint.

The metal instruments of the type described above have the drawback of having to rely mainly on the ability of the surgeon during the operation and of not guaranteeing that the desired intra or extra rotations will be obtained. In particular, slight variations in the positioning of the metal instruments can cause errors with consequent problems in positioning of the prosthesis and in articulation of the knee.

Alternatively, to the solution described above, the distal resection is performed by means of a disposable instrument produced specifically on the basis of the patient's femoral morphology also called PSI, Patient Specific Instrument, for example obtained by means of magnetic resonance imaging, CAT scan or radiography. This instrument is configured also to provide reference holes on the distal bone resection surface which are used for positioning, by means of pins, a metal 4-in-1 cutting jig to guide the sickle blades for execution of the anterior and posterior resection and the anterior and posterior chamfer cuts.

This type of PSI allows a particularly accurate distal cut to be performed according to the femoral morphology of the patient. Furthermore, this instrument allows positioning of the 4-in-1 cutting jig to be guided via the positioning indication of reference pins for positioning said 4-in-1 cutting jig.

However, it is known in literature, for example from:
"Unsatisfactory Accuracy as Determined by Computer Navigation of VISIONAIRE Patient-Specific Instrumentation for Total Knee Arthroplasty"
Sébastien Lustig MD, PhD, b, Corey J. Scholes PhD, Sam I. Oussedik FRCS, Vera Kinzel FRACS a, Myles R. J. Coolican FRACS, David A. Parker FRACS
The Journal of Arthroplasty 28 (2013)
"Patient-specific instrumentation for total knee replacement verified by computer navigation: a case report"
Kok-Yu Chan, Yee-Hong Teo, Department of Orthopaedic Surgery, Tan Tock Seng Hospital, Singapore
Journal of Orthopaedic Surgery 2012; 20
"Patient-specific Total Knee Arthroplasty Required Frequent Surgeon-directed Changes"
Benjamin M. Stronach MD, Christopher E. Pelt MD, Jill Erickson PA, Christopher L. Peters MD
Clin Orthop Relat Res (2013)
"Evaluation of the accuracy of a patient-specific instrumentation by navigation"
Fabio Conteduca, Raffaele Iorio, Daniele Mazza, Ludovico Caperna, Gabriele Bolle, Giuseppe Argento, Andrea Ferretti
Knee Surg Sports Traumatol Arthrosc, 21(2013)
"Component Alignment During Total Knee Arthroplasty with Use of Standard or Custom Instrumentation"
Steven T. Woolson, MD, Alex H. S. Harris, PhD, David W. Wagner, PhD, and Nicholas J. Giori, MD, PhD
THE JOURNAL OF BONE AND JOINT SURGERY, 2014
that incorrect positioning of the PSI distal cutting jig due to incorrect preoperative planning, interference with osteophytes on the femoral surface or simply due to positioning difficulty (the femoral surface is convex, the surface of the PSI jig is concave and there are no particular and easy references for positioning) results in incorrect indication of the references for subsequent positioning of the 4-in-1 jig which determines correct intra- or extra-rotation of the knee.

In order to obtain a desired intra- or extra-rotation of the knee, the surgeon has to manually adjust the inclination of the 4-in-1 cutting jig. Therefore, correct positioning of the 4-in-1 cutting jigs of known type, i.e. correct inclination of the 4-in-1 cutting jig on the distal bone resection surface, relies on the ability of the surgeon during the operation.

Therefore, the known 4-in-1 cutting jig of the type described above has the drawback of not guaranteeing correct positioning to obtain a given intra or extra rotation, with consequent problems, in the event of error, in positioning of the prosthesis and articulation of the knee. Furthermore, it has been found that errors in positioning of the disposable instruments for performance of the distal resection can occur and the 4-in-1 cutting jigs of the type described above do not allow any errors in execution of the distal resection to be indicated and if necessary corrected.

SUMMARY OF THE INVENTION

The object of the present invention is to provide a 4-in-1 cutting jig for femoral finishing which overcomes the problems described above, bypassing the need for landmarks (pin positioning indications) provided by the PSI distal cutting jig (which as illustrated could be incorrect). The cutting jig of the present invention is configured and positioned by means of clear, known and easy-to-use anatomical landmarks, for the purpose of correct positioning.

The purpose of the present invention is to provide a patient-specific 4-in-1 cutting jig for use only after the surgeon has performed the distal resection. In other words, the object of the present invention is to provide a 4-in-1 cutting jig which operates without any connection with the distal cutting operation.

Therefore, advantageously, the object of the present invention is to provide a patient-specific 4-in-1 cutting jig which can equally be combined with mechanical distal cutting instruments, PSI distal cutting jigs and mechanical distal cutting jigs guided by Computer Assisted Surgery navigation systems.

Advantageously, the object of the present invention is to provide a 4-in-1 cutting jig which guarantees a simple/ intuitive mechanical positioning, easy and free from potential errors, based solely on the reference of the posterior condyles and on the distal resection plane according to other methods described above. In other words, the object of the present invention is to provide a 4-in-1 cutting jig that annuls the potential positioning and cutting errors in the surgical phase described in the literature which subsequently require either the need for revision of the surgical procedure to the detriment of conservation of the patient's bone (since the bone cuts have to be recovered again, removing further bone tissue) due to incorrect definition of the intra/extra rotation or, even, a prosthetic revision only a few months after the operation due to incorrect positioning of the prosthetic devices and therefore kinematic failure and consequent replacement of the prosthetic system by means of particularly invasive and debilitating revision surgery.

The object of the invention is to provide a 4-in-1 cutting jig for femoral finishing as claimed in the attached claims.

BRIEF DESCRIPTION OF THE DRAWINGS

The invention will now be described with reference to the attached drawings, which illustrate a non-limiting embodiment example (examples) thereof, wherein:

FIG. 1 is a main view of the distal bone resection surface of a femur;

FIG. 2 is a main view of a 4-in-1 cutting jig according to the present invention applied to the distal bone resection surface of FIG. 1;

DETAILED DESCRIPTION OF THE INVENTION

Figure 3:
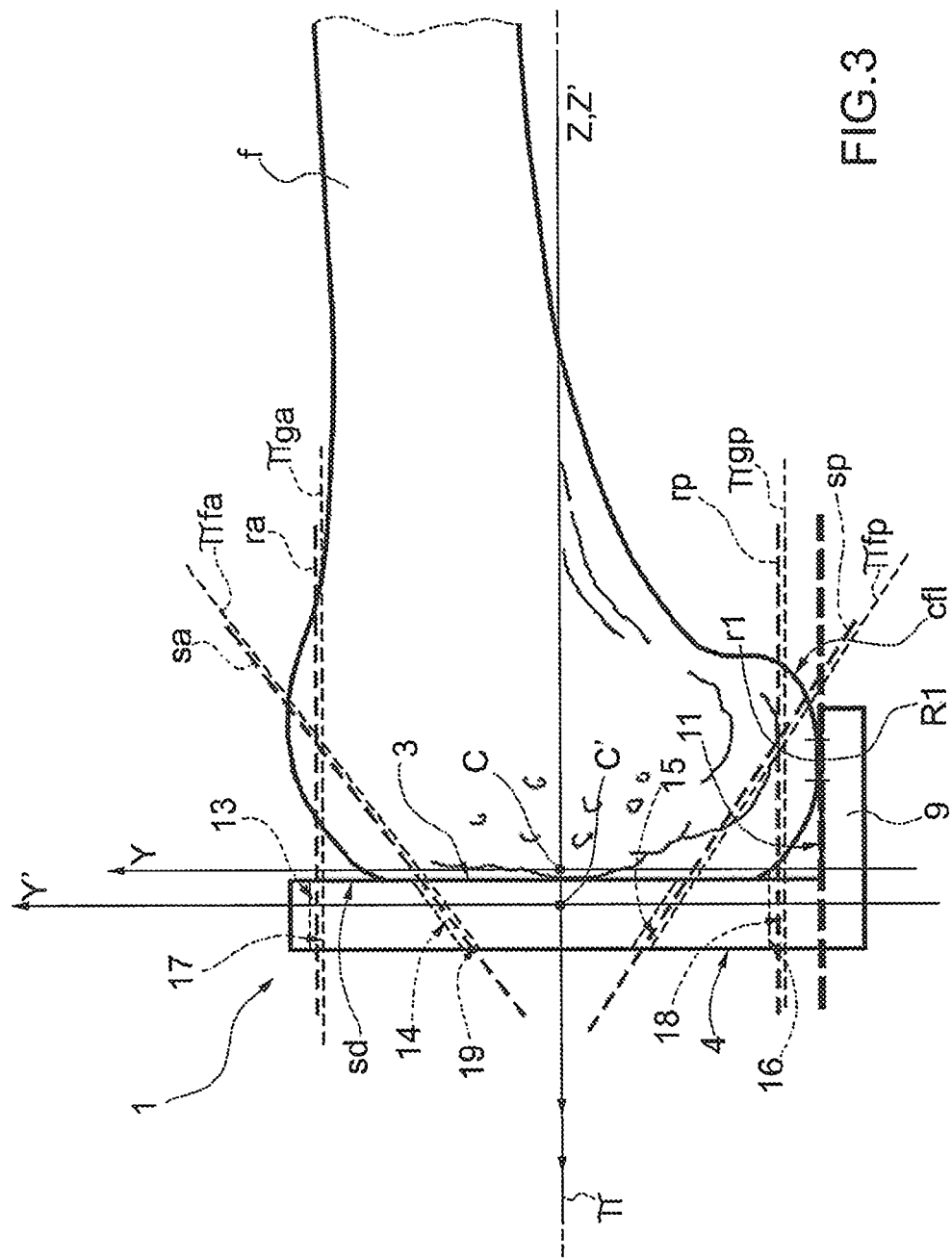
FIG. 3 is a lateral view of FIG. 2.

Below, the terms that represent anatomical references such as distal, proximal, anterior, posterior, medial, lateral, superior and inferior are used with reference to the anatomy of a patient, to the 4-in-1 cutting jig described and to the orthopaedic prostheses. Said terms are well understood and are currently used both in the study of anatomy and in orthopaedics. Therefore, in this discussion the use of said anatomical references is coherent with their well-known meanings, unless explicitly stated otherwise.

In FIG. 1 a femur f is illustrated, in particular a distal resection surface obtained following a distal resection of the femur f. In FIGS. 2 and 3, the number 1 indicates a customised patient-specific 4-in-1 cutting jig for femoral finishing, i.e. a 4-in-1 cutting jig configured to be used on a specific patient during an orthopaedic operation. The jig 1 is a surgical instrument which is used in the operating phase to finish the femur f following distal resection and to promote the implant of a prosthesis. Advantageously, the jig 1 is configured to guide cutting instruments (of known type and not illustrated) during the performance of four different cuts, in particular to perform: anterior resection ra, posterior resection rp, anterior chamfer cut sa and posterior chamfer cut sp.

In particular, the term "4-in-1 cutting jig" refers to a surgical instrument which is applied to the patient only during the operation and is removed for the implant of a prosthesis. Therefore, the jig 1 is distinct from prostheses designed for permanent application on a patient.

The expression "customised and patient-specific" is used to distinguish the 4-in-1 cutting jig according to the present invention from standard instruments that can be re-used on different patients and are not customisable.

The jig 1 is adapted to the morphology of the femur f of the specific patient, in particular it is adapted on the basis of morphological data relative to specific reference landmarks for unequivocal connection to the femur f, as will be illustrated better below. It is observed that a customised patient-specific surgical instrument has one or more surfaces presenting a negative profile configured to receive the corresponding positive profile of a respective bone portion, in this case of the femur f. In this way, the variables depending on the decisions and manual ability of the surgeon during the operation are considerably reduced.

Before arthroplasty, it is known that a preoperative study is carried out to plan the operative procedures to be performed on the patient and to ensure that all the necessary instruments are provided.

In particular, during an investigation phase of the preoperative study, images of the femur f are taken so as to recreate a three-dimensional morphology of the femur f overall. For example, during the investigation phase, it is known that the morphology of the femur f is identified by means of images obtained with computed tomography (CT) such as magnetic resonance imaging (MRI) or computed axial tomography (CAT) or other equivalent technologies. Furthermore, the images of the femur f can be obtained via the use of contrast liquids. In particular, during the investigation phase the exact morphology, i.e. form and dimension, of the femur f is acquired.

Subsequently, on the basis of the information obtained during the investigation phase, an analysis phase is carried out to determine the type of prosthesis that can be applied and, consequently, the type of distal resection and finishing (ra, rp, sa, sp) to be performed on the femur f for implant of the prosthesis. In particular, on the basis of this information it is possible to determine landmarks on the femur f according to which the surgical instruments are positioned, for example the cutting jig 1, during the operation.

In a subsequent phase of preparation of the surgical instruments, this information can be transmitted to a surgical instrument manufacturer who produces customised patient-specific surgical instruments on the basis of the data obtained during the investigation phase. Preferably the data are exchanged with the manufacturer according to the DICOM (Digital Imaging and Communications in Medicine) standard. The manufacturer can use algorithms of known type for management of the images and the creation of three-dimensional models of the femur. In particular, by means of known techniques, the manufacturer is able to determine the contour of the femur f.

On the basis of the morphology of the femur f and type of correction to be made to the joint and/or prosthesis to be implanted, the manufacturer can produce a surgical instrument, in this specific case a 4-in-1 cutting jig 1, the technical specifications of which are defined as a function of the morphology of the femur f and type of anterior ra and posterior rp resection and anterior sa and posterior sp chamfer cuts to be performed to implant the prosthesis.

In particular, for the 4-in-1 cutting jig 1 the manufacturer bases his analysis once the exact position of the distal resection surface sd has been found. In other words, the manufacturer of the 4-in-1 cutting jig 1 prepares the 4-in-1 cutting jig 1 on the basis of the contour of the distal resection surface sd of the femur f.

In this regard, it is observed that different techniques are known for execution of the distal resection of the femur f which guarantee a high accuracy, in other words guaranteeing the creation of reference landmarks positioned around the contour of the femur f also in the preoperative phase.

Therefore, once the position in which to perform the distal resection has been established, the manufacturer is able to define in a unique and precise manner the contour of the distal resection surface sd on the basis of the morphological images of the femur f.

In particular, the manufacturer uses as landmarks the profile of the lateral femoral condyle cfl and the profile of the medial femoral condyle cfm. Furthermore, the manufacturer determines the positioning of three axes X, Y and Z perpendicular to one another and intersecting at a point C. Advantageously, the manufacturer determines: the epicondylar axis X, the anteroposterior axis Y and the posterior condylar axis Z of the femur f.

Advantageously, the jig 1 comprises a cutting block 2 configured to be positioned, in use, in contact with the distal resection surface sd of the femur f of the patient. The block 2 substantially has the shape of a rectangular parallelepiped with axes X', Y' and Z' perpendicular to one another and intersecting at a point C'. The axes X' and Z' and the point C' lie on a common reference plane π.

Advantageously, the axis X' is determined within the block 2 so that it can be overlapped, in use, on the epicondylar axis X. The axis Y' is determined within the block 2 so that it can be overlapped, in use, on the anteroposterior axis Y. The axis Z' can be overlapped, in use, on the posterior condyle axis Z. In use, the points C and C' are coaxial and lie on the axis Z, or Z'.

Using a terminology analogous to the medical terminology also for the jig 1, the block 2 has a proximal surface 3 (illustrated in FIG. 3) configured to be placed in contact, in use, against the distal resection surface sd of the femur f. Furthermore, the block 2 has a distal surface 4 opposite the proximal surface 3, an anterior surface 5, a posterior surface 6, a lateral surface 7 and a medial surface 8. The proximal surface 3 and the distal surface 4 are the surfaces with greatest extension of the block 2. The anterior surface 5 is configured to be positioned, in use, in the vicinity of the anterior part of the femur f. The posterior surface 6 is opposite the anterior surface 5. The lateral surface 7 and medial surface 8 are opposite each other and are perpendicular to the anterior 5, proximal 3, posterior 6 and distal 4 surfaces.

Advantageously, the jig 1 comprises one or more reference elements R, each of which is adapted to be placed in contact with a respective landmark r determined on the femur f of the patient so as to uniquely position the jig 1 with respect to the distal resection surface sd.

Advantageously, the jig 1 comprises a lateral reference element R1 configured to be arranged, in use, in contact with a lateral landmark r1 on the lateral femoral condyle cfl of the patient.

Advantageously, the jig 1 comprises a medial reference element R2 configured to be arranged, in use, in contact with a medial landmark r2 on the medial femoral condyle cfm of the patient.

According to the illustrations of the figures, the jig 1 comprises a lateral contact wall 9, which is configured to be placed in contact with the lateral femoral condyle cfl, and a medial contact wall 10 configured to be placed in contact with the medial femoral condyle cfm.

Advantageously, the lateral contact wall 9 and the medial contact wall 10 project at the rear from the posterior surface 6 of the block and are configured to extend, in use, at least partially along the femur f.

Advantageously, each contact wall 9 and 10 projects from the proximal surface 3 of the block 2 and extends along the axis Z'. In other words, each contact wall 9 and 10 is configured to extend, in use, along the posterior condylar axis Z.

The contact walls 9 and 10 can be flat or have a substantially L-shaped lateral profile. In particular, the largest extension portion of the L extends along the axis Z'.

Each contact wall 9 and 10 is substantially perpendicular to the block 2. The portions of the contact walls 9 and 10 which extend along the axis Z' are substantially parallel to each other.

The contact walls 9 and 10 can be flat (in other words they have a smooth contact surface) and are configured to make contact with a limited substantially point-like area of a respective femoral condyle cfl or cfm. In particular, each contact wall 9 and 10 has a respective lateral 11 and medial 12 contact surface configured to be placed, in use, in contact with the femur f.

Advantageously, the lateral contact surface 11 has a negative profile configured to house, in use, the positive profile of the lateral femoral condyle cfl.

The distance d1' along the axis Y' between the lateral contact surface 11 and the axis X' is a function of the morphology of the femur f of the patient. In particular, the distance d1' corresponds to the distance d1 along the anteroposterior axis Y between the lateral landmark r1 and the epicondylar axis X.

Advantageously, the medial contact surface 12 has a negative profile configured to house, in use, the positive profile of the medial femoral condyle cfm.

The distance d2' along the axis Y' between the medial contact surface 12 and the axis X' is a function of the morphology of the femur f of the patient. In particular, the distance d2' corresponds to the distance d2 along the anteroposterior axis Y between the medial landmark r2 and the epicondylar axis X.

The block 2 has four guides, each of which is configured to guide, in use, a cutting instrument for performing the anterior ra and posterior rp resections and the anterior sa and posterior sp chamfer cuts (schematized by broken lines in FIG. 3).

Advantageously, the block 2 has: an anterior guide 13 for the anterior resection ra; an anterior slot 14 for the anterior chamfer cut sa; a posterior slot 15 for the posterior chamfer cut sp; and a posterior guide 16 for the posterior resection rp.

The anterior guide 13 is a through guide, i.e. it extends through the entire cutting block 2 and establishes communication between the proximal surface 3 and the distal surface 4 of the block 2. The anterior guide 13 is rectilinear and extends along the axis X'. According to the illustrations of FIGS. 2 and 3, the anterior guide 13 has a guide surface 17 configured to be placed, in use, in contact with a cutting instrument, for example a sickle blade (of known type and not illustrated). According to the example illustrated in FIGS. 2 and 3, the guide surface 17 of the anterior guide 13 is parallel to the reference plane π.

According to a variation, not illustrated, the plane πga (illustrated schematically in FIG. 3) on which the guide surface 17 lies and the reference plane π are incident.

Advantageously the inclination of the guide surface 17 (in other words the inclination of the plane πga) relative to the reference plane π is a patient-specific datum and is a function of the morphology of the femur f of the patient and of the type of prosthesis to be applied.

Advantageously, the angle of the guide surface 17 around the axis X' is determined so as to regulate the quantity of the bone material of the femur f to be removed.

Advantageously, the angle of the guide surface 17 around the axis Z' is determined so as to impart a desired intra or extra rotation of the joint.

Analogously, the posterior guide 16 is a through guide, i.e. it extends through the entire block 2 and establishes communication between the proximal surface 3 and the distal surface 4 of the block 2. The posterior guide 16 is rectilinear and extends along the axis X'. According to the illustrations of FIGS. 2 and 3, the posterior guide 16 has a guide surface 18 which is configured to be placed, in use, in contact with a cutting instrument, for example a sickle blade (of known type and not illustrated). According to the example illustrated in FIGS. 2 and 3, the guide surface 18 of the posterior guide 16 is parallel to the reference plane $\pi$.

According to a variation not illustrated, the plane $\pi$gp on which the guide surface 18 lies and the reference plane $\pi$ are incident.

Advantageously the inclination of the guide surface 18 relative to the reference plane $\pi$ is a patient-specific datum and is a function of the morphology of the femur f of the patient and the type of prosthesis to be applied.

Advantageously, the angle of the guide surface 18 around the axis X' is determined so as to regulate the quantity of bone material of the femur f to be removed.

Advantageously, the angle of the guide surface 18 around the axis Z' is determined so as to impart a desired intra or extra rotation to the joint of the prosthesis to be implanted.

The anterior slot 14 is a through slot, i.e. it extends through the entire cutting block 2 and establishes communication between the proximal surface 3 and the distal surface 4 of the block 2. The anterior slot 14 is rectilinear and extends along the axis X'. According to the illustrations of FIGS. 2 and 3, the anterior slot 14 has a slot surface 19 which is configured to be placed, in use, in contact with a cutting instrument, for example a sickle blade (of known type and not illustrated). According to the illustrations of FIGS. 2 and 3, the slot surface 19 of the anterior slot 14 lies on a plane $\pi$fa incident with the reference plane $\pi$.

Advantageously the inclination of the slot surface $\pi$fa relative to the reference plane $\pi$ is a patient-specific datum and is a function of the morphology of the femur f of the patient and the type of prosthesis to be applied.

Advantageously, the angle between the slot surface 19 and the reference plane $\pi$ around the axis X' is determined so as to regulate the quantity of bone material of the femur f to be removed.

Advantageously, the angle of the slot surface 19 around the axis Z' is determined so as to impart a desired intra or extra rotation to the joint.

The posterior slot 15 is a through slot, i.e. it extends through the entire block 2 and establishes communication with the proximal surface 3 and the distal surface 4 of the block 2. The posterior slot 15 is rectilinear and extends along the axis X'. According to the illustrations of FIGS. 2 and 3, the posterior slot 15 has a slot surface 20 which is configured to be placed, in use, in contact with a cutting instrument, for example a sickle blade (of known type and not illustrated). The slot surface 20 of the posterior slot 15 lies on a plane $\pi$fp incident with the reference plane $\pi$.

Advantageously the inclination of the slot surface 20 relative to the reference plane $\pi$ is a patient-specific datum and is a function of the morphology of the femur f of the patient and of the type of prosthesis to be applied.

Advantageously, the angle between the slot surface 20 and the reference plane $\pi$ around the axis X' is determined so as to regulate the quantity of bone material of the femur f to be removed.

Advantageously, the angle of the slot surface 20 around the axis Z' is determined so as to impart a desired intra or extra rotation to the joint.

Advantageously, the relative arrangement along the axis Y' of the anterior guide 13, of the anterior slot 14, of the posterior slot 15 and of the posterior guide 16 is patient-specific and is a function of the morphology of the femur f of the patient and/or of the type of prosthesis to be implanted.

Advantageously, the jig 1 is made of a material adapted to be used in contact with organic tissues. In particular, the jig 1 is made of a material configured to undergo the sterilization procedures in autoclave for surgical operations or ethylene oxide, plasma or gamma ray sterilization. Advantageously, the jig 1 is made of anallergic material. For example, the jig 1 is made, at least partly, of plastic material. In particular, the jig 1 is made, at least partly, of polymer materials such as polyamide, poly (phenylsulphone) or polyketone. For example, the jig 1 is made of nylon (PA2200 polyamide).

The jig 1 can be produced by means of a 3D printing system, for example by means of a laser sintering process.

Advantageously, the block 2 of the jig 1 has a plurality of holes 21, each of which is a through hole and is configured to guide pins or equivalent elements, of known type and not illustrated, configured to fix in a known manner the jig 1 on the distal resection surface sd of the femur f.

According to a variation not illustrated, each or some of the guides 13 and/or 16 and the slots 14 and/or 15 of the type described above are provided inside bodies mounted slidingly, in a known manner, along the axis X', of known type and not illustrated, which allow the guide of the cutting instrument to be prolonged also in lateral areas external to the block 2.

In use, during the operation the surgeon performs, according to the data obtained from the preoperative phase, distal resection of the femur f using known technologies and so as to create the distal resection surface sd.

The jig 1 is then applied on the distal resection surface sd. During the phase of applying the jig 1, the reference elements (R; R1, R2) of the jig 1 are arranged in contact with predefined landmarks (r; r1, r2) of the femur f. In particular, during the application phase, the lateral contact wall 9 is placed against the respective lateral landmark r1 on the lateral femoral condyle cfl, while the medial contact wall 10 is placed against the respective medial landmark r2 on the medial femoral condyle cfm.

In particular, the lateral contact wall 9 is arranged so that the negative profile of its lateral contact surface 11 coincides with the corresponding positive profile of the respective lateral femoral condyle cfl. Analogously, the medial contact wall 10 is arranged with the negative profile of its medial contact surface 12 in contact with the corresponding positive profile of the respective medial femoral condyle cfm.

Advantageously, the lateral and medial contact walls 9 and 10 extend along the femur f, in particular along the posterior condylar axis Z, and are configured to be placed in contact with an extensive area of the femur f.

Alternatively, the reference landmarks (r; r1, r2) of the femur f are limited and almost point-like surfaces. Therefore, the lateral 9 and medial 10 contact walls are placed against said surfaces.

The lateral 9 and medial 10 contact walls allow the jig 1 to be uniquely arranged above the distal resection surface sd of the femur f.

Advantageously, the jig 1 is applied above the distal resection surface sd so that the inclination of the anterior and posterior 16 guides and of the anterior 14 and posterior 15 slots is unique and as determined in the preoperative phase. In other words, the jig 1 of the type described above, due to the lateral 9 and medial 10 contact walls which engage against the lateral cfl and medial cfm femoral condyle respectively, allows arrangement of the anterior 13 and posterior 16 guides and of the anterior 14 and posterior 15 slots with the exact inclinations (in particular around the axis X' and Z') determined in the preoperative phase and with the exact arrangement along the axis X'.

Lastly, the jig 1 is fixed, in a known manner, to the distal resection surface sd by means of pins inserted in the holes 21.

Subsequently, the resection operations are performed by inserting cutting instruments, for example sickle blades, inside the guides and slots so as to complete execution of the anterior and posterior resection and the anterior and posterior chamfer cuts.

Lastly, the pins and the cutting jig are removed to allow the implant of a prosthesis.

From the above, it follows that the cutting jig of the type described above drastically reduces, and even eliminates, the possibility of error during the operative phase due to incorrect positioning of the cutting jig relative to the distal resection surface sd or incorrect adjustment of the inclination of the guides or slots to impart an intra or extra rotation to the joint of the prosthesis.

It is highlighted that advantageously, the lateral femoral condyle cfl and the medial femoral condyle cfm represent more stable and reliable supporting surfaces for an instrument like the 4-in-1 cutting jig 1 of the type described above since they are advanced with respect to the front view of the femur. At the front, on the other hand, the surface of the femur does not represent such a reliable base since it is more oblique and receding and the positioning of a 4-in-1 jig would be more laborious, less user-friendly and could generate more errors.

The choice of the lateral cfl and/or medial cfm femoral condyles as reference elements guarantees the correctness and stability of the positioning of the jig 1 of the type described above.

Furthermore, the jig 1 of the type described above is quick and simple to use as the lateral femoral condyle cfl and the medial femoral condyle cfm represent easily identifiable landmarks. The customization of the jig 1 of the type described above as a function of the morphology of the femur f of the patient furthermore facilitates insertion and positioning of the jig 1.

Lastly, the jig 1 of the type described above can be stably fixed to the distal resection surface sd and allows the unique positioning to be maintained throughout the operation.

The invention claimed is:

1. A customized patient-specific 4-in-1 femoral finishing cutting jig, comprising:
   a cutting block that has a proximal surface which is configured to be placed, in use, in contact with a distal resection surface of a femur;
   a reference means that is configured to position, in use, the cutting block relative to the distal resection surface in a predetermined and patient-specific manner;
   wherein the reference means includes a first contact element having a first flat surface that is configured to face, in use, a first femoral condyle and being customized and patient-specific, the first flat surface is configured to be placed in contact with a respective customized and patient-specific landmark which is a limited and almost point-like surface identified on a respective portion of the first femoral condyle; and
   the reference means includes a second contact element having a second flat surface that is configured to face, in use, a second femoral condyle and being customized and patient-specific, the second flat surface is configured to be placed in contact with a respective customized and patient-specific landmark which is a limited and almost point-like surface identified on a respective portion of the second femoral condyle; and
   the first and the second flat surface are parallel to each other, substantially perpendicular to the cutting block, and have a different distance from an epicondylar axis of the femur which is customized and patient-specific.

2. The customized patient-specific 4-in-1 femoral finishing cutting jig according to claim 1, wherein the distance between each contact element and an epicondylar axis of the femur is customized and patient-specific; the distance between the first contact element and the epicondylar axis is substantially equal to the distance between the first landmark and the epicondylar axis itself; the distance between the second contact element and the epicondylar axis is substantially equal to the distance between the second landmark and the epicondylar axis itself.

3. The customized patient-specific 4-in-1 femoral finishing cutting jig according to claim 1, wherein the block has distributed along a first axis substantially parallel to the antero-posterior axis of the femur;
   an anterior guide having a first guide surface that is configured to guide, in use, a cutting instrument during performance of an anterior resection;
   an anterior slot having a second guide surface that is configured to guide, in use, a cutting instrument during performance of an anterior chamfer cut;
   a posterior slot having a third guide surface that is configured to guide, in use, a cutting instrument during performance of a posterior chamfer cut; and
   a posterior guide having a fourth guide surface that is configured to guide, in use, a cutting instrument during performance of a posterior resection.

4. The customized patient-specific 4-in-1 femoral finishing cutting jig according to claim 3, wherein the arrangement along the first axis of the anterior guide, anterior slot, posterior slot, and posterior guide is customized and patient-specific.

5. The customized patient-specific 4-in-1 femoral finishing cutting jig according to claim 3, wherein the inclination of at least one of the first, second, third, or fourth guide surface relative to a reference plane around a second axis substantially parallel to the epicondylar axis of the femur are customized and patient-specific.

6. The customized patient-specific 4-in-1 femoral finishing cutting jig according to claim 3, wherein the inclination of at least one of the first, second, third, or the fourth guide surface relative to a reference plane around a third axis substantially parallel to a posterior condylar axis of the femur are customized and patient-specific.

7. The customized patient-specific 4-in-1 femoral finishing cutting jig according to claim 1, wherein the cutting block is made of a plastic material.

8. The customized patient-specific 4-in-1 femoral finishing cutting jig according to claim 1, wherein the customized patient-specific 4-in-1 femoral finishing cutting jig is manufactured by 3D printing.

* * * * *